United States Patent
Saeed Malik

(10) Patent No.: US 10,143,810 B2
(45) Date of Patent: Dec. 4, 2018

(54) NEEDLE GUIDE

(71) Applicant: Muhammad Zubair Saeed Malik, Tampa, FL (US)

(72) Inventor: Muhammad Zubair Saeed Malik, Tampa, FL (US)

( * ) Notice: Subject to any disclaimer, the term of this patent is extended or adjusted under 35 U.S.C. 154(b) by 69 days.

(21) Appl. No.: 15/076,899

(22) Filed: Mar. 22, 2016

(65) Prior Publication Data
US 2017/0274158 A1     Sep. 28, 2017

(51) Int. Cl.
*A61M 5/46* (2006.01)
*A61M 5/32* (2006.01)
*A61M 5/42* (2006.01)

(52) U.S. Cl.
CPC ............ *A61M 5/46* (2013.01); *A61M 5/3287* (2013.01); *A61M 5/427* (2013.01)

(58) Field of Classification Search
CPC .......... A61B 17/1721; A61B 5/150748; A61B 8/4209; A61B 8/0841; A61B 17/3403; A61B 90/11; A61B 2017/3405; A61B 2017/3407; A61M 5/427
See application file for complete search history.

(56) References Cited

U.S. PATENT DOCUMENTS

| | | | | |
|---|---|---|---|---|
| 2,451,183 A | * | 10/1948 | Tantimonaco | A61B 5/15003 604/115 |
| 2,697,433 A | * | 12/1954 | Zehnder | A61B 17/1703 606/103 |
| 3,135,263 A | * | 6/1964 | Connelley, Jr. | A61B 90/11 33/512 |
| 4,733,661 A | * | 3/1988 | Palestrant | A61B 17/3403 128/DIG. 26 |
| 4,883,053 A | * | 11/1989 | Simon | A61B 17/3403 606/130 |
| 5,201,742 A | * | 4/1993 | Hasson | A61B 17/3403 606/1 |
| 5,280,427 A | * | 1/1994 | Magnusson | A61B 90/10 600/407 |
| 5,308,352 A | * | 5/1994 | Koutrouvelis | A61B 17/3403 604/116 |
| 5,665,095 A | * | 9/1997 | Jacobson | A61B 90/11 604/116 |
| 5,941,889 A | * | 8/1999 | Cermak | A61B 8/0833 606/130 |
| 7,736,371 B2 | * | 6/2010 | Schoepp | A61B 17/3403 604/104 |
| 8,241,301 B2 | * | 8/2012 | Zhang | A61B 90/11 600/407 |
| 8,430,889 B2 | * | 4/2013 | Zeng | A61B 17/3403 606/1 |
| 8,517,985 B2 | * | 8/2013 | Wei | A61M 5/46 604/117 |
| 8,758,300 B2 | | 6/2014 | Bakhtyari-Nejad-Esfahani | |

(Continued)

*Primary Examiner* — Scott Medway
(74) *Attorney, Agent, or Firm* — Dunlap Bennett & Ludwig PLLC

(57) ABSTRACT

A needle guide formed of a base plate and a platform is provided. The base plate includes an upper surface, a lower surface, a front end, a rear end, a first side, a second side, an outer edge and an inner edge. The inner edge forms an opening in between. The platform is pivotally secured to the base plate and disposed over the opening. A locking mechanism is operable to lock the platform at different angles relative to the base plate.

9 Claims, 4 Drawing Sheets

(56) References Cited

U.S. PATENT DOCUMENTS

| | | | |
|---|---|---|---|
| 8,945,011 B2* | 2/2015 | Sheldon | A61B 17/3403 600/417 |
| 9,232,977 B1* | 1/2016 | Rehman | A61B 90/11 |
| 9,655,686 B2* | 5/2017 | Lee | A61B 90/11 |
| 2003/0055436 A1* | 3/2003 | Daum | A61B 90/11 606/130 |
| 2005/0033315 A1* | 2/2005 | Hankins | A61B 90/11 606/129 |
| 2005/0267373 A1 | 12/2005 | Lee | |
| 2006/0229641 A1* | 10/2006 | Gupta | A61B 17/3403 606/130 |
| 2007/0038113 A1* | 2/2007 | Oonuki | A61B 8/0833 600/464 |
| 2009/0112084 A1* | 4/2009 | Piferi | G01R 33/286 600/421 |
| 2009/0143684 A1* | 6/2009 | Cermak | A61B 8/0841 600/461 |
| 2009/0171184 A1* | 7/2009 | Jenkins | A61B 5/7435 600/411 |
| 2010/0168766 A1* | 7/2010 | Zeng | A61B 17/3403 606/130 |
| 2011/0190787 A1* | 8/2011 | Sahni | A61B 19/201 606/130 |
| 2012/0265098 A1* | 10/2012 | McGhie | A61M 5/008 600/567 |
| 2013/0066232 A1* | 3/2013 | Schoepp | A61B 17/3403 600/567 |
| 2015/0157787 A1 | 6/2015 | Cully et al. | |
| 2016/0128719 A1* | 5/2016 | Cermak | A61B 8/0841 600/461 |
| 2017/0128098 A1* | 5/2017 | Lee | A61B 17/3403 |

\* cited by examiner

NEEDLE GUIDE

BACKGROUND OF THE INVENTION

The present invention relates to a needle guide and, more particularly, to a needle guide that provides additional accuracy.

Vascular access is a general term to describe where blood is removed from and returned to the body during HD. A vascular access may be an arteriovenous (AV) fistula, an AV graft, or a catheter. An AV fistula is the preferred type of vascular access because it causes fewer problems with infection and clotting. Catheters have the most problems with infection.

An arteriovenous (AV) fistula is an abnormal connection between an artery and a vein. Normally, blood flows from your arteries to your capillaries to your veins. Nutrients and oxygen in your blood travel from your capillaries to tissues in your body. With an arteriovenous fistula, blood flows directly from an artery into a vein, bypass. To access AV fistula for Hemodialysis, two needles are inserted.

A needle biopsy is a procedure to obtain a sample of cells from your body for laboratory testing. Common needle biopsy procedures include fine-needle aspiration and core needle biopsy. Needle biopsy may be used to take tissue or fluid samples from muscles, bones, and other organs, such as the liver or lungs.

Currently, it is very difficult to guide a needle or catheter with a precise angle and depth.

As can be seen, there is a need for a needle guide that guides a needle or catheter at the proper angle and depth.

SUMMARY OF THE INVENTION

In one aspect of the present invention, a needle guide comprises: a base plate comprising an upper surface, a lower surface, an outer edge and an inner edge, wherein the inner edge forms an opening in between; a platform pivotally secured to the base plate and disposed over the opening, wherein the platform comprises a plurality of pivoted positions, wherein each of the pivoted positions comprises the platform disposed at a different angle relative to the upper surface of the base plate; and a locking mechanism operable to lock the platform in each of the plurality of pivoted positions.

These and other features, aspects and advantages of the present invention will become better understood with reference to the following drawings, description and claims.

DETAILED DESCRIPTION OF THE INVENTION

Figure 1:
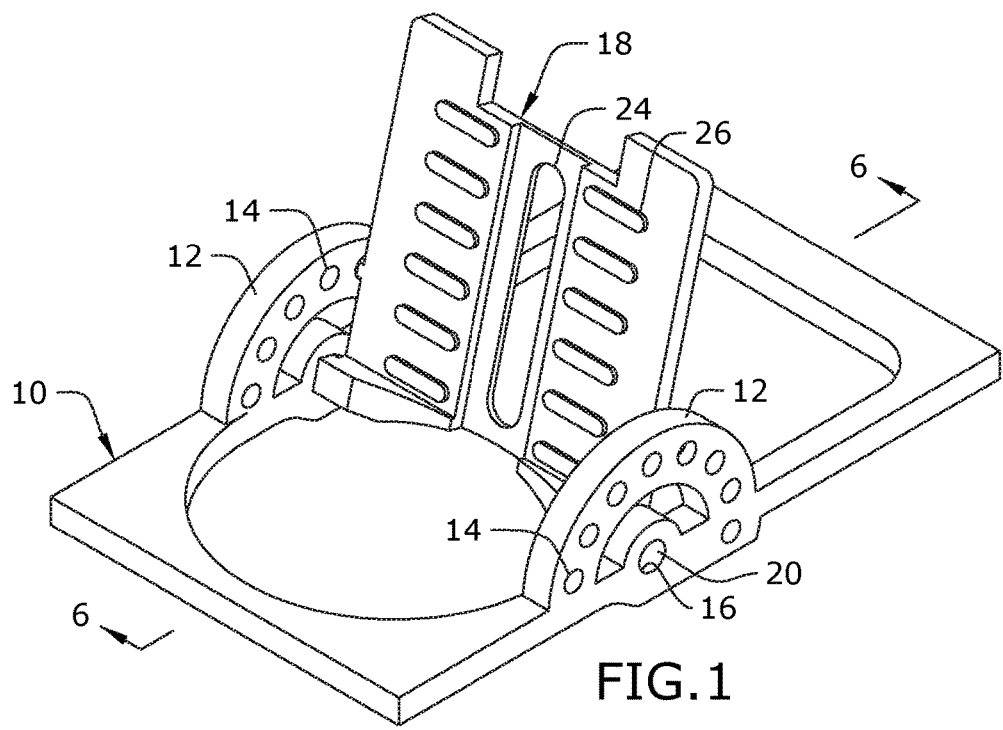
FIG. 1 is a front perspective view of an embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a needle guide that aids in precisely accessing blood vessels and body organs using a needle. The present invention can be used to access arteriovenous fistula, veins, perform kidney biopsy and the like. The present invention may include a base and a platform. The base provides stability and the angle of the platform may be altered for the specified procedure. Additionally, the platform provides support to needle. If it is used to access arteriovenous fistula it will prevent Infiltration of AV fistulas and provide stability. If the present invention is used to do a body organ biopsy e.g. Kidney Biopsy under CT scan then the present invention provides an accurate angle and control to perform the biopsy.

The needle guide of the present invention is placed onto the arm and over an arterio-venous fistula (AVF) or arterio-venous graft (AVG), in order to insert a needle into an entry point at a certain angle, depth and direction. The needle guide can be secured to the arm and left in position to secure the needle and hold it in the proper position during a dialysis procedure, without rotating the needle (often the plan for deep fistulas). Alternatively, the needle guide can be held in place during needle insertion and then removed so the needle can be rotated, advanced and secured to the skin (as with more superficial fistulas).

The angle and depth of insertion of needles into entry points is critical to the success of cannulation of an access vessel. This is especially true for fistulas that are somewhat small in diameter, deep in the SQ tissue, or varying in depth and angle. The present invention allows users to determine for example, a 30 degree angle of insertion or 15 mm depth of penetration below the skin. In buttonhole tract development. it is especially vital to have the initial sharp needles and later blunt needles later inserted at the exact angle and depth for each insertion.

The following are some of the advantages of the needle guide device. The present invention allows for ease in training users how to insert a needle into an insertion point at a specific angle in relation to the skin and to a specified depth. The present invention assures that subsequent insertions follow the same prescribed angle and depth. The present invention improves the fixation of the needle after insertion, especially for needles in deep fistulas that will not be rotated. The present invention minimizes infiltration of the access area due to needle movement or improper insertion. The present invention assures more accurate insertion of sharp and blunt needles during development of buttonhole tracts in fistulas.

Figure 2:
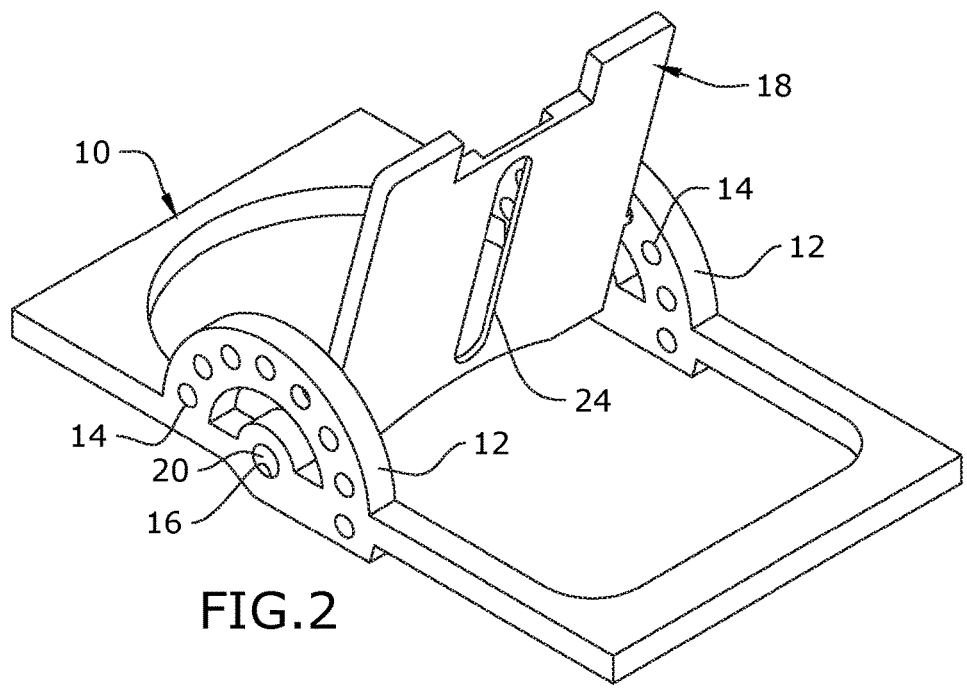
FIG. 2 is a rear perspective view of an embodiment of the present invention.
Figure 3:
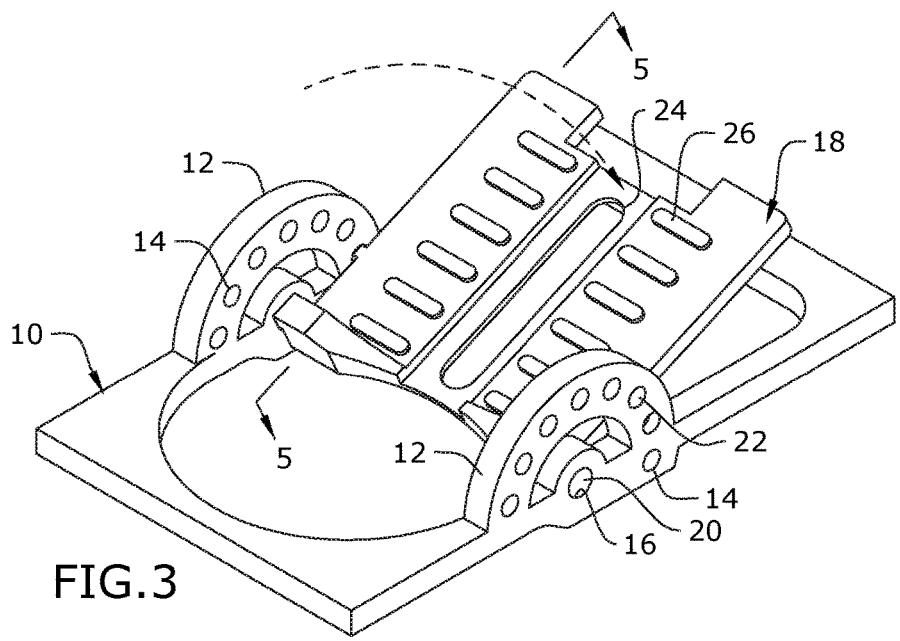
FIG. 3 is a front perspective view of an embodiment of the present invention shown in an exemplary secondary configuration.
Figure 4:
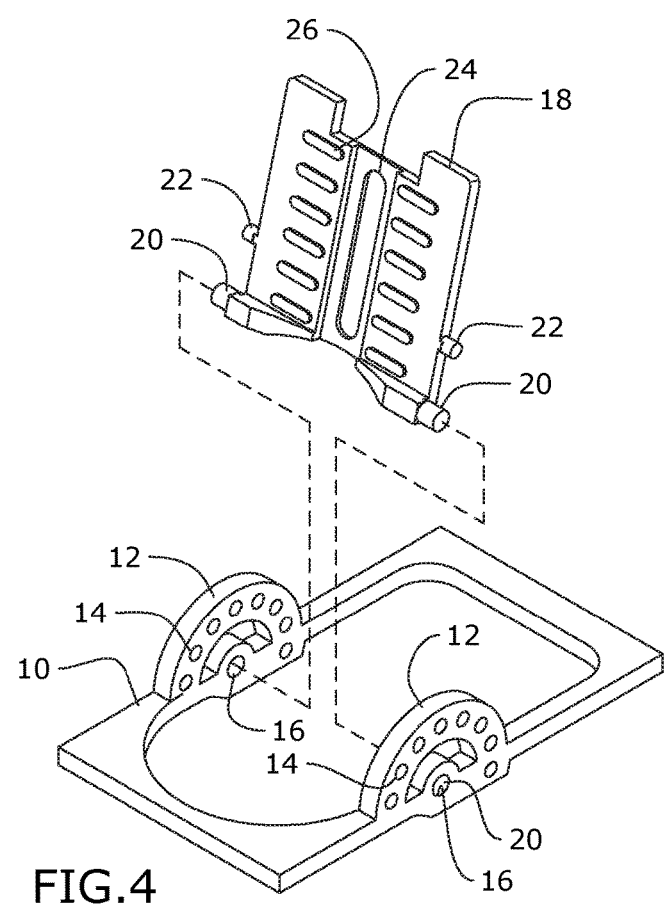
FIG. 4 is an exploded view of an embodiment of the present invention.
Figure 5:
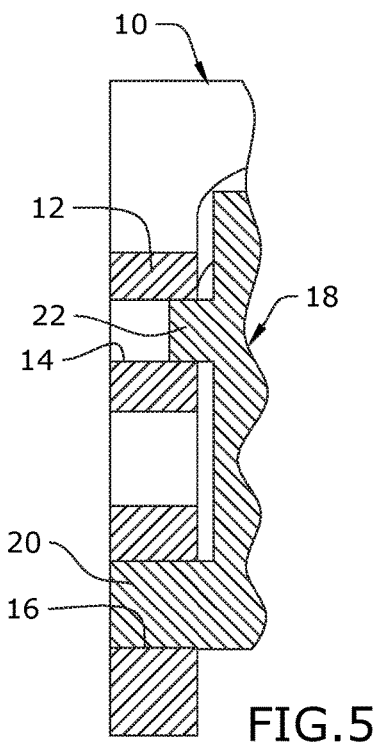
FIG. 5 is a section detail view of the present invention taken along 5-5 in FIG. 3 demonstrating the pivoting interface.
Figure 6:
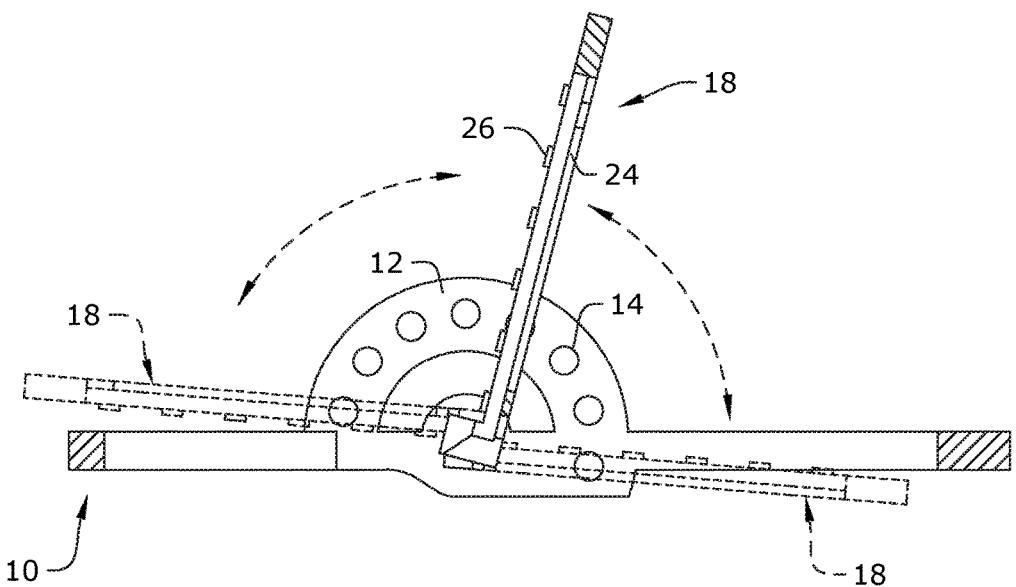
FIG. 6 is a section view of the present invention taken along line 6-6 in FIG. 1 demonstrating full range of motion.
Figure 7:
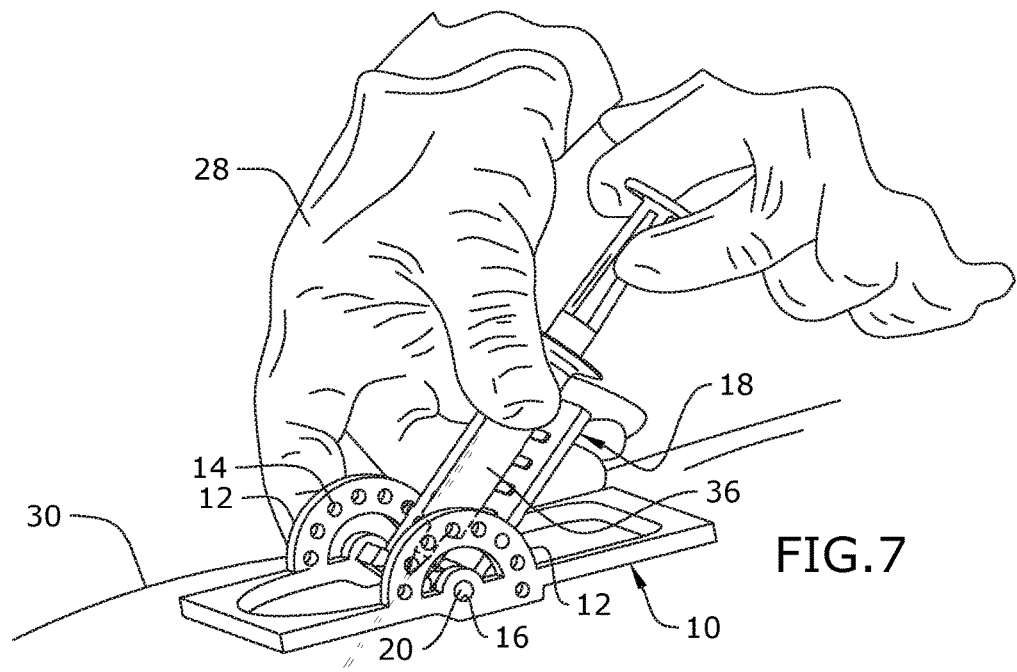
FIG. 7 is a perspective view of an embodiment of the present invention shown in use.
Figure 8:
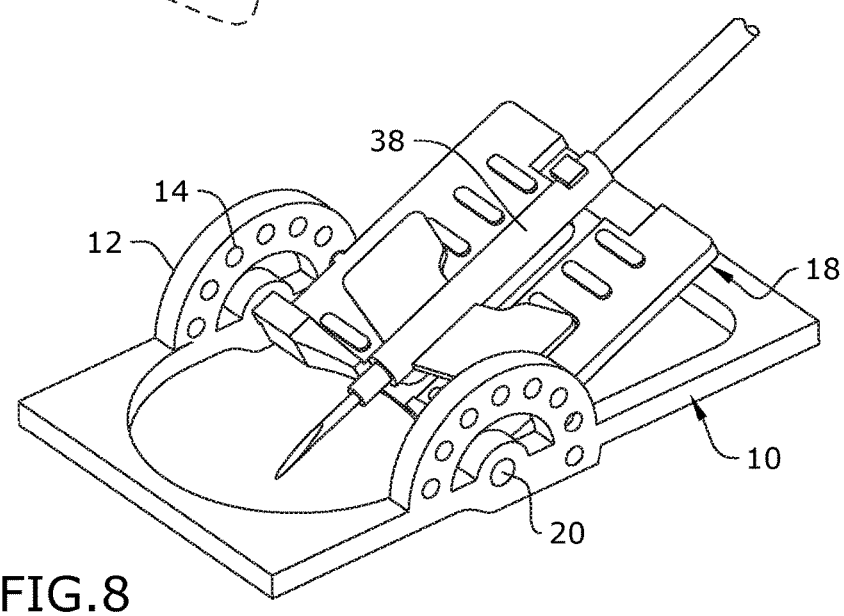
FIG. 8 is a perspective view of an embodiment of the present invention shown in use.

Referring to FIGS. 1 through 8, the present invention includes a needle guide formed of a base plate 10 and a platform 18. The base plate 10 includes an upper surface, a lower surface, a front end, a rear end, a first side, a second side, an outer edge and an inner edge. The inner edge forms an opening in between. The platform 18 is pivotally secured to the base plate 10 and disposed over the opening. The platform 18 may pivot from the front end to the rear end of the base plate 10, thereby pivoting from 0 degrees to 180 degrees relative to the upper surface of the base plate 10. A locking mechanism is operable to lock the platform 18 at different angles relative to the base plate 10.

The base plate 10 of the present invention may include a substantially planar upper surface and a substantially planar lower surface. The base plate 10 provides support when placed against a patient 30. The base plate 10 may be made of a sturdy material, such as a hard plastic, aluminum and the like. As mentioned above, the base plate 10 includes an opening formed in between the inner edge. The opening may be sized so that the needle may run through opening when disposed at different angles.

In certain embodiments, the platform 18 is pivotally connected to the base plate 10 via pivot pegs 20 and pivot openings 16. For example, the base plate 10 may include a pivot opening 16 formed through the inner edge on the first side and the second side. The platform 18 may include pivot pegs 20 extending laterally from a bottom portion. The pivot pegs 20 fit and rotate within the pivot openings 16. Therefore, the platform 18 is able to pivot from the front end to the rear end of the base plate 10.

The locking mechanism of the present invention may include any locking mechanism that locks the platform 18 relative to the base plate 10 so that the platform 18 may no longer pivot. In certain embodiments, a locking protrusion 12 may be formed on the first side of the upper surface and the second side of the upper surface. The locking protrusion 12 may be a semi-circular shape. The locking protrusions 12 may include a plurality of first mating connectors 14. A second mating connector 22 extends from opposing sides of the platform 18 and connects with the first mating connectors 14, locking the platform 18 in place. For example, the first mating connectors 14 may include apertures and the second mating connectors 22 may include a mating peg sized to fit within each of the apertures. The plurality of apertures formed through the locking protrusion 12 may align in the shape of an arc, allowing the platform 18 to lock at different angles relative to the base 10, In certain embodiments, a channel 24 is formed on a front surface of the platform 18. The channel 24 runs from a top end to a bottom end of the platform 18. The channel 24 is sized to receive a portion of either a needle 36 or a catheter 38 when the needle guide is in use. A slot may be formed within the channel 24. The front surface of the platform 18 may further include plurality of depth marks 26 disposed along the channel 24. The plurality of depth marks 24 may include centimeter units.

To use the present invention, the platform 18 may be pivoted to an angle relative to the upper surface of the base 12 and then locked in place via the locking mechanism. An operator 28 may place the base 12 on a patient 30 to target an organ 34. The channel 24 may be placed right above the desired insertion target of the patient 30. The operator 28 may then place the needle 36 or catheter 38 along the channel 24 and insert the needle into the patient's skin. Using the present invention, the operator 28 may precisely inject the needle 36 at the desired injection target.

It should be understood, of course, that the foregoing relates to exemplary embodiments of the invention and that modifications may be made without departing from the spirit and scope of the invention as set forth in the following claims.

What is claimed is:

1. A needle guide comprising:
   a base plate comprising a flat upper surface, a lower surface an outer edge, and an inner edge, wherein the flat upper surface comprises a front end, a rear end opposite the front end, a first side, and a second side opposite the first side, wherein a distance from the first side to the second side is greater than a distance from the flat upper surface to the lower surface, the inner edge defines an opening and a locking protrusion is coupled to and extending from each of the first side and the second side of the flat upper surface of the base plate such that each of the locking protrusions are perpendicular to the flat upper surface, wherein each of the locking protrusions comprises a plurality of first mating connectors, the plurality of first mating connectors of one of the locking protrusions corresponds with the plurality of first mating connectors of the other of the locking protrusions;
   a flat platform pivotally secured to the base plate at the first side and the second side in between from front end and the rear end such that the flat platform is capable of pivoting above the flat upper surface from the rear end to the front end over the opening, the flat platform comprising a second mating connector extending from each of opposing sides of the flat platform, wherein the flat platform comprises a plurality of pivoted positions, the pivoted positions each comprising the second mating connectors connected with different corresponding first mating connectors of the plurality of first mating connectors so that the flat platform is locked in place at a different angle relative to the flat upper surface of the base plate.

2. The needle guide of claim 1, wherein the flat platform is pivotally secured to the base plate by pivot pegs protruding from a bottom end of the flat platform and disposed within pivot openings formed through the base plate.

3. The needle guide of claim 1, wherein the plurality of corresponding first mating connectors comprises pairs of apertures and the second mating connectors each comprise a mating peg sized to fit within each of the apertures.

4. The needle guide of claim 1, wherein the plurality of corresponding first mating connectors align to form an arc shape on each of the locking protrusions.

5. The need guide of claim 1, further comprising a channel formed on a front surface of the flat platform, wherein the channel runs from a top end to a bottom end of the flat platform.

6. The needle guide of claim 5, further comprising a slot formed within the channel.

7. The needle guide of claim 5, further comprising a plurality of depth marks disposed on the front surface of the flat platform along the channel.

8. The needle guide of claim 7, wherein each of the plurality of depth marks indicates a centimeter of length.

9. The needle guide of claim 1, wherein the different angles range from 0 degrees up to 180 degrees.

* * * * *